(12) United States Patent  (10) Patent No.: US 8,806,921 B2
Gosling et al.  (45) Date of Patent: Aug. 19, 2014

(54) VISCOMETER AND A METHOD FOR OPERATING THE SAME

(75) Inventors: Stephen J. Gosling, Sonderborg (DK); Ian Mylrea, Essex (GB)

(73) Assignee: Poulten Selfe & Lee Ltd., Essex (GB)

( * ) Notice: Subject to any disclaimer, the term of this patent is extended or adjusted under 35 U.S.C. 154(b) by 502 days.

(21) Appl. No.: 12/774,985

(22) Filed: May 6, 2010

(65) Prior Publication Data

US 2010/0281956 A1  Nov. 11, 2010

Related U.S. Application Data

(60) Provisional application No. 61/176,019, filed on May 6, 2009.

(30) Foreign Application Priority Data

May 6, 2009  (EP) .................................... 09159545

(51) Int. Cl.
*G01N 11/04*  (2006.01)

(52) U.S. Cl.
USPC ........................................................ 73/54.04

(58) Field of Classification Search
USPC ...................................................... 73/54.04
See application file for complete search history.

(56) References Cited

U.S. PATENT DOCUMENTS

| 3,699,804 | A | * | 10/1972 | Gassmann et al. | 73/54.07 |
| 3,713,328 | A | * | 1/1973 | Aritomi | 73/54.08 |
| 3,981,182 | A | * | 9/1976 | Kossler et al. | 73/54.08 |
| 4,028,929 | A | * | 6/1977 | Bohm | 73/54.04 |
| 4,583,395 | A | * | 4/1986 | Anantaraman | 73/54.04 |
| 5,224,375 | A | * | 7/1993 | You et al. | 73/54.08 |
| 5,946,921 | A | * | 9/1999 | Mapes et al. | 62/85 |
| 6,286,360 | B1 | * | 9/2001 | Drzewiecki | 73/24.01 |
| 6,698,216 | B2 | * | 3/2004 | Goth et al. | 62/150 |
| 2003/0014983 | A1 | * | 1/2003 | Maisotsenko et al. | 62/121 |

FOREIGN PATENT DOCUMENTS

| DE | 2442943 | A1 |   | 4/1975 |
| GB | 1418431 | A |   | 12/1975 |
| GB | 1418431 | A | * | 12/1975 |
| GB | 2255644 | A |   | 11/1992 |

\* cited by examiner

*Primary Examiner* — Hezron E Williams
*Assistant Examiner* — Mark A Shabman
(74) *Attorney, Agent, or Firm* — Muncy, Geissler, Olds & Lowe, P.C.

(57) ABSTRACT

A viscometer adapted to determine a temperature at which a liquid test sample has a predetermined viscosity. A method of operating a viscometer comprising the steps of: drying the air contained in the capillary tube; advancing the liquid test sample from the sample reservoir to the capillary tube; changing the temperature of the liquid test sample to a first sub-zero degrees Celsius temperature, and determining a first viscosity of the liquid test sample at the first sub-zero degrees Celsius temperature. Use of a capillary tube for determining a temperature at which a liquid test sample has a predetermined viscosity.

15 Claims, 5 Drawing Sheets

VISCOMETER AND A METHOD FOR OPERATING THE SAME

This application claims priority of U.S. Provisional Application No. 61/176,019, filed on May 6, 2009 under 35 U.S.C. §119(e), the entire contents of all of which are hereby incorporated by reference.

FIELD OF THE INVENTION

The present invention relates to a viscometer. Moreover, the present invention relates to a method of operating a viscometer. Finally the present invention relates to the use of a viscometer.

BACKGROUND OF THE INVENTION

Aeroplanes operate in very low temperature environments, mainly due to the altitude which they fly but also due to low temperatures on the ground in colder climates. Especially, extreme conditions may occur at high altitude in Polar Regions. As the fuel temperature decreases, the viscosity increases, and may reach a critical viscosity where the fuel becomes difficult to atomise. This may cause the fuel to be difficult or even impossible to ignite. Moreover, the fuel in the fuel tanks may during flying be cooled down to a temperature at which the viscosity of the fuel exceeds a pumpability limit, thus making it impossible to deploy the fuel to the engines.

Thus, it is common practice to select the aviation fuel by one or more standardized criteria set by specification and standardization authorities for aviation fuels. The criterion is that the viscosity of the aviation fuel must be below a predetermined level when measured at a temperature of e.g. minus 20 degrees Celsius.

It has surprisingly been found that drying the inner surfaces with compressed air so as to remove any solvent used to clean the viscometer between tests, is not sufficient to obtain a valid measurement. The reason is that although the solvent has been removed, air contained inside the capillary assembly during cooling thereof, causes dew to be formed on the inner surfaces of the capillary assembly as the moisture in the air reaches its dew point and condenses on the inner surface of the capillary tube. Moreover, the dew may form ice crystals on the inner surface of the capillary assembly when the temperature is lowered to a temperature below zero degrees Celsius. The formed ice makes the measurements with the capillary assembly unrealisable.

Furthermore, it has surprisingly been found that using a test for filterability is not suitable for determining quality of e.g. an airplane fuel, as a sample with high cloud and pour points may block a filter ahead of a more viscous sample which contains little or no wax and consequently does not block the filter.

Accordingly, it is an object of embodiments of the present invention to provide an improved method for determining whether the aviation fuel is suitable for use e.g. in extreme conditions.

Moreover, it is an object of embodiments of the present invention to prevent formation of dew and ice crystals on the inner surface of the capillary assembly.

BRIEF DESCRIPTION OF THE INVENTION

In a FIRST aspect the present invention relates to a viscometer adapted to determine a temperature at which a liquid test sample has a predetermined viscosity.

In the context of the present invention the term "viscosity" shall be understood as a measure of the resistance of a fluid which is being deformed by either shear stress or extensional stress. Accordingly the larger the resistance to flow is, the more viscous the liquid is.

In some embodiments, the viscosity determined by means of the apparatus or method of the present invention is the kinematic viscosity. The relationship between the viscosity and the kinematic viscosity is as follows:

viscosity=kinematic viscosity*density of the liquid

It is noted that not only will the viscometer be capable of determining the temperature at which the liquid test sample has a predetermined viscosity, it may also in some embodiments be capable of determining the viscosity at a predetermined temperature. This could be at a temperature of minus 20 degrees Celsius. Accordingly, the apparatus according to the present invention may also be used to perform the test which today is prescribed by the aviation fuel specification and standardization authorities i.e. the test in which the viscosity at minus 20 degrees Celsius is determined. Alternatively, or as a supplement the test may be carried out at a temperature of minus 40 degrees Celsius and/or at a temperature of plus 20 degrees Celsius The viscometer may be adapted to perform tests on liquid test samples which have a temperature above and/or below zero degrees Celsius. In one embodiment, the temperature, at which the predetermined viscosity is determined, is a sub-zero degrees Celsius temperature, such as a temperature below minus 20 degrees Celsius, such as a temperature below minus 30 degrees Celsius, such as a temperature below minus 40 degrees Celsius, such as a temperature below minus 50 degrees Celsius.

In one embodiment, the temperature—at which the predetermined viscosity is determined—is a temperature below the dew point of the air surrounding the apparatus, e.g. the air in the room or laboratory in which the viscometer is located. The dew point in the context of the present invention is the temperature to which the air must be cooled for water vapour to condense into water.

In one embodiment, the viscometer comprises a hygrometer for determining the humidity of the air contained in the capillary assembly and/or a hygrometer for determining the humidity of the air surrounding the viscometer. Moreover, the viscometer may be adapted to determine the dew point of the air on the basis of the temperature and the humidity of the air in the test area—e.g. the capillary assembly or the surrounding air.

It will be appreciated that for a predetermined amount of water vapour in the air (e.g. in the capillary assembly), the humidity increases the lower the temperature of this air is. Thus when the capillary assembly is used at sub-zero degrees Celsius temperatures, it is vital that the amount of water vapour in the air in the capillary assembly is reduced prior to cooling of the capillary assembly in order to avoid that dew is formed on the inner surfaces of the capillary assembly. Accordingly, the viscometer may in some embodiments be adapted to determine/predict how low the amount of vapour in the capillary assembly must be in order to avoid that the air condenses on the inner surface of the capillary assembly.

In one embodiment, the viscometer comprises:
- a capillary assembly comprising a capillary tube and/or a timing bulb;
- a sample reservoir fluidly connected to the capillary assembly;
- an air drying apparatus arranged to dry air in the capillary assembly;

a pump for advancing the liquid test sample from the sample reservoir to the capillary assembly; and an apparatus for controlling the temperature of the liquid test sample.

In one embodiment, at least one of the capillary tube and the timing bulb—in use—is oriented such that the liquid test sample contained in the capillary tube and/or the timing bulb is allowed to flow by gravity. As an example the capillary tube and/or the timing bulb may be oriented in a substantially vertical manner.

The capillary may be transparent and may contain a transparent material such as glass or plastic. The capillary may be adapted to be removed and reinstalled in the viscometer e.g. so as to allow the capillary to be removed for cleaning.

In one embodiment, the temperature of the 'apparatus for cooling' remains at a sub-zero degrees Celsius temperature during operation, whereby the capillary tube must be moved out of the 'apparatus for cooling' in order to elevate the temperature of the capillary to a temperature above zero degrees Celsius e.g. during cleaning of the capillary. In the same embodiment, the capillary is cooled down by lowering the capillary into the apparatus for cooling.

In another embodiment, the temperature of the 'apparatus for cooling' is elevated to a temperature above the dew point of the ambient air.

The capillary assembly, the sample reservoir and an interconnecting tube for fluidly connecting the capillary assembly and the sample reservoir may form one single element such as a monolithic element (i.e. one single element without seams). As an example, the three elements may form one single glass element.

The pump for advancing the liquid test sample from the sample reservoir to the capillary assembly may be arranged such that the liquid test sample is pushed into the capillary assembly. This effect may be achieved by providing the pump such that it generates an increased pressure in the sample reservoir which thus causes the liquid test sample to flow into the capillary tube via the interconnecting tube.

Alternatively, the pump may be arranged to suck the liquid test sample from the sample reservoir into the capillary assembly. This effect may be achieved by providing a reduced pressure in the capillary assembly.

In one embodiment, the viscometer comprises two pumps one which is arranged to provide the increased pressure in the sample reservoir as is described above, and another which is arranged to provide the reduced pressure in the capillary assembly.

In one embodiment, the apparatus for controlling the temperature comprises a container adapted to contain a temperature controlling medium. A liquid medium for controlling the temperature may be provided in the container and, thus, the container must be liquid tight. Examples of such a medium is a low viscosity liquid which remains in its liquid state at low temperatures e.g. down to minus 50 degrees Celsius. The low viscosity liquid may be transparent to visible light and/or infrared light and/or ultraviolet light. Examples of low viscosity liquids are ethanol, silicone oils, mineral oils and glycols. Alternatively, the container is air tight and a gas is used to cool or heat the liquid test sample during use of the viscometer. Examples of such gasses are air and inert gasses such as nitrogen and argon. It will be appreciated that such gasses may be dried before use, so as to prevent it from forming dew in the outer surfaces of the capillary assembly.

In one embodiment, the capillary tube and/or the sample reservoir may be arranged to be movable into and out of the container. In the latter embodiment, the capillary tube and/or the sample reservoir may be moved out of the container during removal of the test liquid and/or during cleaning.

The air drying apparatus may be arranged to circulate air in the capillary tube when no liquid test sample is contained in the capillary tube. In one embodiment, the capillary tube comprises a venting tube which may be fluidly connected to and/or in direct physically connected with a lower part of the capillary tube such that when a venting pump is operated, the air in the capillary tube is circulated into the venting tube. From the venting tube the air may be ventilated into a means for drying the air, and subsequently reintroduced into the capillary assembly. Examples of such means for drying the air are desiccant dryers, refrigerated dryers, deliquescent dryers and membrane driers.

The viscometer may comprise a controller e.g. a micro processor comprising a memory unit. The viscometer may be adapted to perform (e.g. by means of a controller):

a first step:
in which the air drying apparatus is operated so as to dry air contained in the capillary tube, and
in which the pump is operated so as to advance the liquid test sample from the sample reservoir to the capillary tube; and a second step:
in which the apparatus for controlling the temperature of the liquid test sample is operated so as to change the temperature of the liquid test sample to a first sub-zero degrees Celsius temperature, and
in which a first viscosity of the liquid test sample at the first sub-zero degrees Celsius temperature is determined.

The air drying apparatus may be operated until a predetermined humidity is obtained. Alternatively, the air drying apparatus may be operated until the humidity cannot be lowered further by means of the air drying apparatus. In the latter case, the air drying apparatus may be operated until the humidity has not decreased for a predetermined period of time such as for a period of 30 seconds or 1 minute or 2 minutes or 5 minutes or ten minutes. It will be appreciated that by reducing the humidity as much as possible, the risk of condensation on the inner surfaces of the capillary assembly, is reduced as much as possible.

The pump for advancing the liquid test sample may be operated until the liquid test sample has reached a predetermined position in the capillary tube. This position may be a position above the below described upper position. During operation of the pump, the ventilation tube may be closed so as to prevent the liquid test sample from entering said tube. In one embodiment, a valve interconnects the capillary tube and the venting tube. In other embodiments, the valve may be positioned in the middle or top of the venting tube such as in the transition between the venting tube and the means for drying the air.

Moreover, a valve or any other suitable means may be provided for retaining the liquid test sample in the capillary tube, e.g. while the apparatus for controlling the temperature is operated.

In one embodiment, the first sub-zero degrees Celsius temperature may be minus 20 degrees Celsius, such as minus 30 degrees Celsius, such as minus 40 degrees Celsius. A thermometer may be arranged to determine the temperature of the liquid test sample e.g. by being provided in the capillary assembly or in the sample reservoir.

Alternatively, or as a supplement, a thermometer may be provided for determining the temperature in the 'apparatus for controlling the temperature' e.g. in a temperature controlling liquid in the previously mentioned container. Once the predetermined temperature has been reached, the viscosity of the liquid test sample may be determined.

In one embodiment, an upper and a lower detector may be provided at an upper and a lower position of the timing bulb, respectively. When the meniscus of the liquid test sample passes the upper detector a first point in time is determined, and when the meniscus of the liquid test sample passes the lower detector a second point in time is determined. The first and second points in time may be stored in the memory of the processor. Based on information about the volume of the capillary assembly between the upper and lower positions and the time difference between the first and second points in the time, the viscosity may be calculated. The processor may be adapted to perform said calculation.

The processor may comprise a data processor, a memory which may be used to store information about the abovementioned volume and to store the first and second points in time.

As the air drying apparatus is operated in order to prevent dew to form on the inner surface of the capillary tube e.g. during cooling to a sub-zero degrees Celsius temperature, the air drying apparatus may (in the first step) be operated while the temperature of the capillary tube is above the dew point of the air contained in the capillary tube. The processor may be adapted to determine the dew point based on information about the humidity of the air in the capillary assembly and the temperature of the air and/or the capillary assembly. Alternatively, or as a supplement, the viscometer may be adapted to determine the dew point of the air surrounding the viscometer.

If the first viscosity is not the predetermined viscosity, the controller may be adapted to perform a third step:
  in which the air drying apparatus is operated so as to dry air contained in the capillary tube, and
  in which the pump is operated so as to advance the liquid test sample from the sample reservoir to the capillary tube; and a fourth step:
  in which the apparatus for controlling the temperature of the liquid test sample is operated so as to change the temperature of the liquid test sample to a second sub-zero degrees Celsius temperature, and
  in which a second viscosity of the liquid test sample at the second sub-zero degrees Celsius temperature is determined.

In one embodiment, the controller is adapted to operate the pump so as to advance the liquid test sample into the capillary assembly before operating the apparatus for controlling the temperature so as to change the temperature of the liquid test sample. The effect is that the liquid test sample is advanced into the capillary assembly before the temperature of the capillary assembly is changed. When the viscometer is operated at sub-zero degrees Celsius temperatures this provides the advantage that the air contained in the capillary assembly is displaced by the liquid test sample, and is thus prevented from condensing in the area which is now occupied by the liquid test sample. This increases the accuracy of the test result.

If the viscosity determined at the first sub-zero degrees Celsius temperature is above the predetermined viscosity, the temperature of the liquid test sample is raised during the fourth step. This is done in order to reach a temperature at which the viscosity is at the predetermined level.

If, on the contrary the viscosity at the first sub-zero degrees Celsius temperature is lower than the predetermined viscosity, the temperature of the liquid test sample is lowered during the fourth step. Again the temperature is changed in order to reach a viscosity which is at the predetermined level.

In both cases the temperature is changed to the second sub-zero degrees Celsius temperature at which the second viscosity is determined.

If this second sub-zero degrees Celsius temperature does also not result in a measurement of the predetermined viscosity, the third and fourth steps may be repeated at different sub-zero degrees Celsius temperatures until the predetermined viscosity is determined. However, will be appreciated that after the measurement at the second sub-zero degrees Celsius temperature, the temperature of the liquid test sample is changed to a third sub-zero degrees Celsius temperature at which a third viscosity is determined. If the third viscosity is not equal to the predetermined viscosity, the temperature is changed to a fourth sub-zero degrees Celsius temperature and a fourth viscosity is determined and so on. The process is continued until the temperature is determined at which the viscosity is at the predetermined level (i.e. 'the determined viscosity'='the predetermined viscosity').

The controller may be adapted to determine the temperature at which the next measurement is to be carried out in order to reach the temperature at which the viscosity is at the predetermined level.

This can be done in a plurality of different ways:

In a first simple embodiment, a linear relationship between the temperature and the viscosity is assumed and the next temperature at which a measurement is to be carried out is predicted by means of such a simple linear function.

In a second embodiment, a non-linear relationship between the temperature and the viscosity is assumed and the next temperature at which a measurement is determined is predicted by means of such a non-linear function.

In a third embodiment, the viscosity is determined at predetermined temperature intervals. As an example the temperature may be lowered by five or ten degrees Celsius between each measurement of the viscosity e.g. such that the viscosity is determined at the following temperatures: minus 20 degrees Celsius, minus 30 degrees Celsius, minus 40 degrees Celsius, minus 50 degrees Celsius etc.

In a fourth embodiment, the viscosity is determined at predetermined temperatures (which contrary to the third embodiment need not be separated by the same predetermined number of degrees Celsius). As an example the viscosity may be determined at the following temperatures: minus 20 degrees Celsius, minus 40 degrees Celsius, minus 42 degrees Celsius, minus 44 degrees Celsius, minus 46 degrees Celsius, minus 47 degrees Celsius, minus 48 degrees Celsius, minus 49 degrees Celsius and minus 50 degrees Celsius.

In a fifth embodiment, the user loads a function into the controller prior to the test, which function represents the relationship between the temperature and the viscosity.

In a sixth embodiment, the user loads information into the controller relating to the type of liquid. Examples are the type of crude oil from which the liquid emanates and/or the information about the location of the oil rig by means of which liquid was drilled and/or the name of the distillery/refinery at which the liquid was distilled/refined and/or whether the liquid is based on natural and/or synthetic oil. Other examples are physical properties of the liquid e.g. the density, the freeze point, the lubricity, the flash point, the sulphur content, the distillation characteristics (e.g. the initial boiling temperature; the temperature with 10 percent recovery, 20 percent recovery, 50 percent recovery or 90 percent recovery; the final boiling point). Other properties may be found in the Defence Standard 91-91 of 8 Apr. 2008 'Turbine fuel, Aviation Kerosine Type, Jet A-1, NATO Code: F-35, Joint Service Designation: AVTUR' by Ministry of Defence of the United Kingdom.

It will be appreciated that the controller may be programmed to perform any combination of the above. As an example the controller may be adapted to use initiate the process by determining the temperature at minus 20 degrees Celsius and at minus 40 degrees Celsius (i.e. at predetermined intervals of minus 20 degrees Celsius) and subsequently use a linear or a non-linear method to determine further temperatures at which the viscosity is measured.

In a SECOND aspect, the present invention relates to a method of operating a viscometer which comprises a capillary assembly (which may comprise a capillary tube and/or a timing bulb), a sample reservoir fluidly connected to the capillary tube, an air drying apparatus arranged to dry air in the capillary tube, a pump for advancing the liquid test sample from the sample reservoir to the capillary tube, and an apparatus for controlling the temperature of the liquid test sample, the method comprising the steps of:

drying the air contained in the capillary assembly;
advancing the liquid test sample from the sample reservoir to the capillary assembly;
changing the temperature of the liquid test sample to a first sub-zero degrees Celsius temperature, and
determining a first viscosity of the liquid test sample at the first sub-zero degrees Celsius temperature.

As the first and second aspect of the present invention relates to the same general inventive concept, the invention according to the second aspect may comprise any combination of features and elements of the invention of the first aspect, and vice versa.

In one embodiment, the step of drying the air is performed while the capillary assembly is above the dew point of air contained in the capillary assembly. This may be done in order to prevent dew from forming on the inner surface of the capillary assembly when the capillary assembly is cooled down.

As was explained under the first aspect of the invention, the predetermined viscosity may not be measured at the first sub-zero degrees Celsius temperature (i.e. in the first attempt). Accordingly, the method may further comprise the steps of:

drying the air contained in the capillary assembly;
(re-)advancing the liquid test sample from the sample reservoir to the capillary assembly; and
changing the temperature of the liquid test sample to a second sub-zero degrees Celsius temperature, and
determining a second viscosity of the liquid test sample at the second sub-zero degrees Celsius temperature.

Again, the step of advancing the liquid test sample may precede the step of changing the temperature. This provides the advantage that the air displaced by the liquid test sample is prevented from forming dew in the area from which it was displaced.

Moreover, as the temperature at which the liquid test sample has the predetermined may neither be the first nor the second sub-zero degrees Celsius temperatures, further measurements may be performed at different temperatures (third temperatures, fourth temperatures etc.). Accordingly, the steps of drying, (re-)advancing, changing the temperature and determining a third (fourth etc.) viscosity may be repeated at different sub-zero degrees Celsius temperatures until the predetermined viscosity is determined.

It has been found by the inventors that cleaning the capillary assembly at sub-zero degrees Celsius temperatures does not lead to a satisfactory result. The reason for this could be that the viscosity at sub-zero degrees Celsius temperatures is relatively high whereby the resistance of the liquid test sample and/or the cleaning liquid to flow is too high. Accordingly, it may be difficult to remove the sample and the cleaning liquid. Moreover, the solubility of the test medium may be lower at low temperatures than at higher temperatures. Accordingly, the method may further comprise the steps of:

raising the temperature of the capillary assembly;
removing the liquid test sample from the capillary assembly; and
cleaning the capillary assembly.

In one embodiment, the step of raising precedes the step of removing.

In one embodiment, the temperature (the cleaning temperature) may be a temperature above zero degrees Celsius. In another embodiment, the cleaning is performed when the capillary assembly is at a temperature above the dew point of the ambient air. In yet another embodiment, the temperature of the capillary assembly elevated to a temperature above 50 degrees Celsius, such as above 70 degrees Celsius, such as above 80 or 100 degrees Celsius.

In one embodiment, the step of determining the viscosity comprises the steps of:

releasing the liquid test sample such that it flows down through the capillary assembly under gravity;
determining a first point in time at which the meniscus of the liquid test sample passes a first (upper) test position;
determining a second (lower) point in time at which the meniscus of the liquid test sample passes a second test position; and
determining the viscosity on the basis of the first and second points in time and information about the volume of the capillary tube between the first and second positions.

In a THIRD aspect the present invention relates to the use of a capillary tube for determining a temperature at which a liquid test sample has a predetermined viscosity.

BRIEF DESCRIPTION OF THE FIGURES

The invention will now be described with reference to the figures in which.

DETAILED DESCRIPTION OF THE INVENTION

Figure 1:
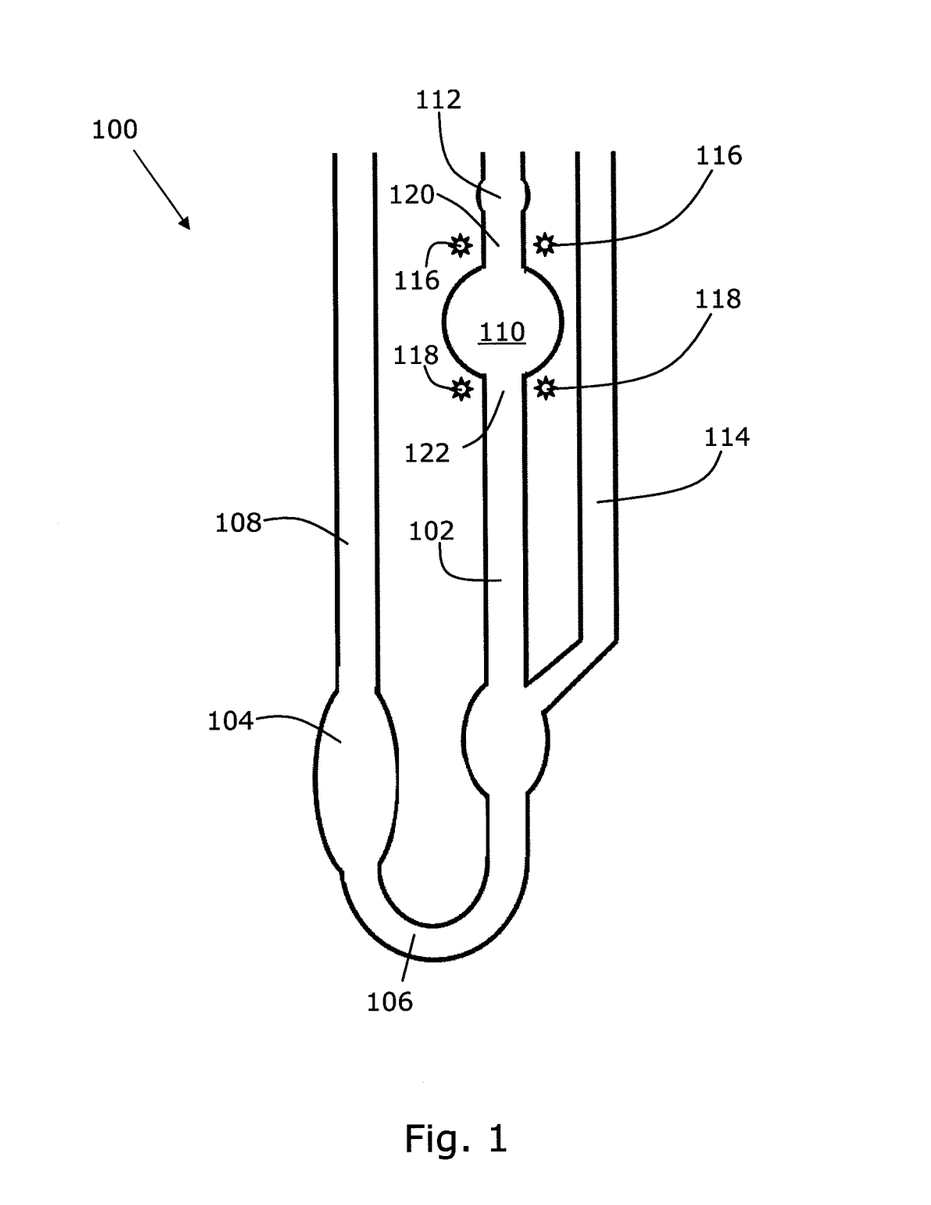
FIG. 1 discloses a principal sketch of the capillary assembly, the sample reservoir, the interconnecting tube and the venting tube, FIG. 2 discloses a liquid test sample accommodated in the sample reservoir and the interconnecting tube, FIG. 3 discloses drying the air in the capillary assembly, FIG. 4 discloses advancing of the liquid test sample into the capillary assembly, and FIG. 5 discloses testing of the viscosity of the liquid test sample.

FIG. 1 discloses a viscometer 100 comprising capillary tube 102 which is fluidly connected to a sample reservoir 104 by means of an interconnecting tube 106. In order to allow a liquid test sample to be filled into the sample reservoir 104, the sample reservoir 104 is connected to a filling tube 108. Moreover, the capillary tube 102 may form part of a capillary assembly which also comprises a timing bulb 110. The timing bulb 110 is fluidly connected to an overfill bulb 112. A venting tube 114 is fluidly connected to the capillary tube 102. In order to determine the viscosity, an upper sensor 116 and a lower sensor 118 are arranged such that they can determine the passage of the meniscus at a first/upper position 120 and a second/lower position 122, respectively. The upper position 120 is provided above the timing bulb 110 and the lower position 122 is provided below the timing bulb 110.

In embodiments, where the sensors 116,118 are optical sensors it will be understood that it is desirable that the capillary assembly is transparent so as to allow light to be transmitted through the capillary assembly. However, the sensors may also be non-optical. Examples of such non-optically based sensors are proximity sensors, conductance sensors and thermocouple sensors.

An embodiment of the method and an embodiment of the apparatus according to the present invention are illustrated in FIGS. 2-5. As the final product may comprise a plurality of different valves, tubes, pumps etc., the drawings have been simplified in order to increase the readability of the figures. As an example the pump 126 is only disclosed in FIG. 3.

Figure 2:
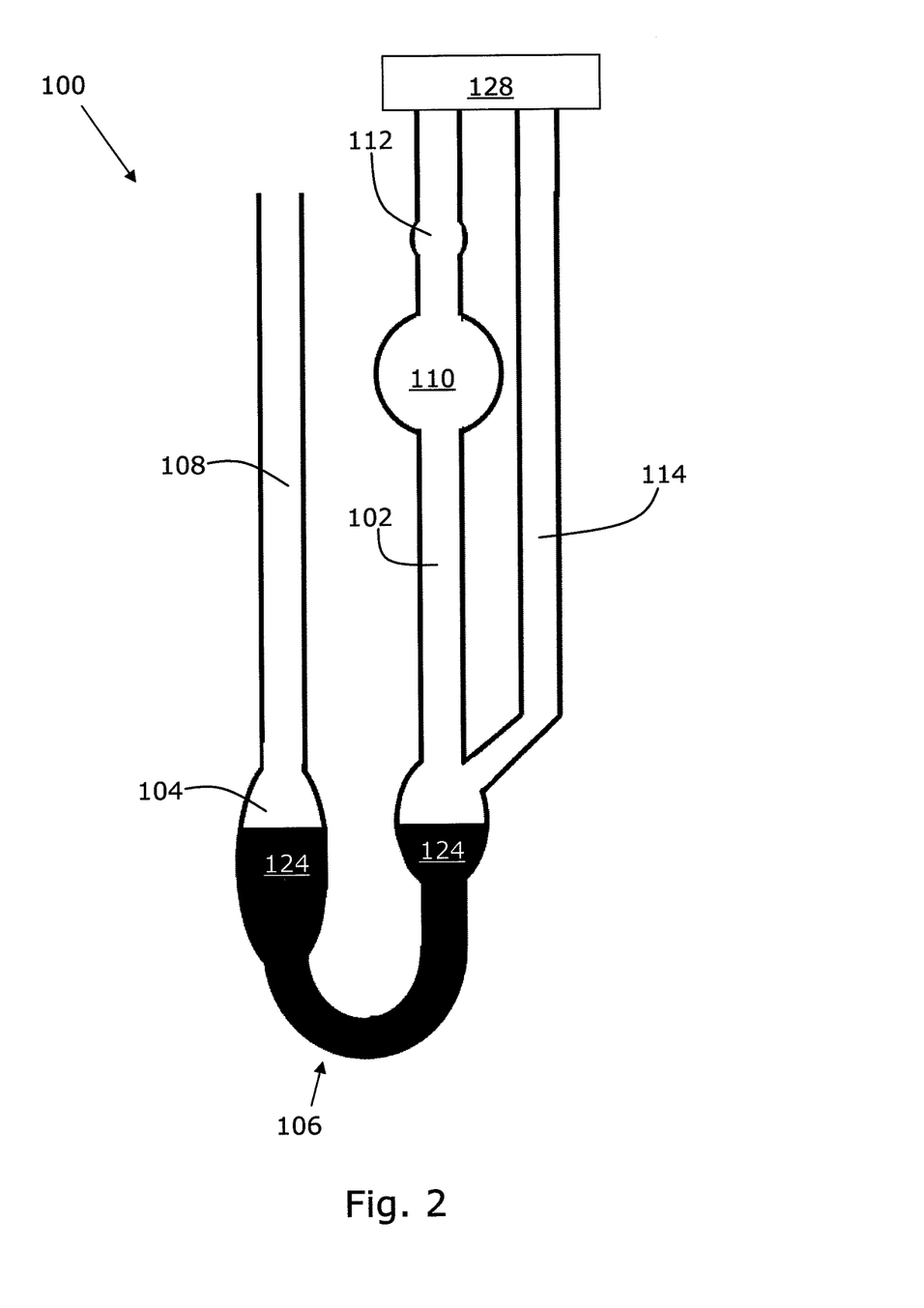

Initially the liquid test sample 124 is poured into the filling tube 108 from which it flows into the sample reservoir 104 and the interconnecting tube 106. This is illustrated in FIG. 2. In one embodiment, the viscometer 100 comprises a funnel (not illustrated) for filling the liquid test sample into the filling tube 108.

Figure 3:
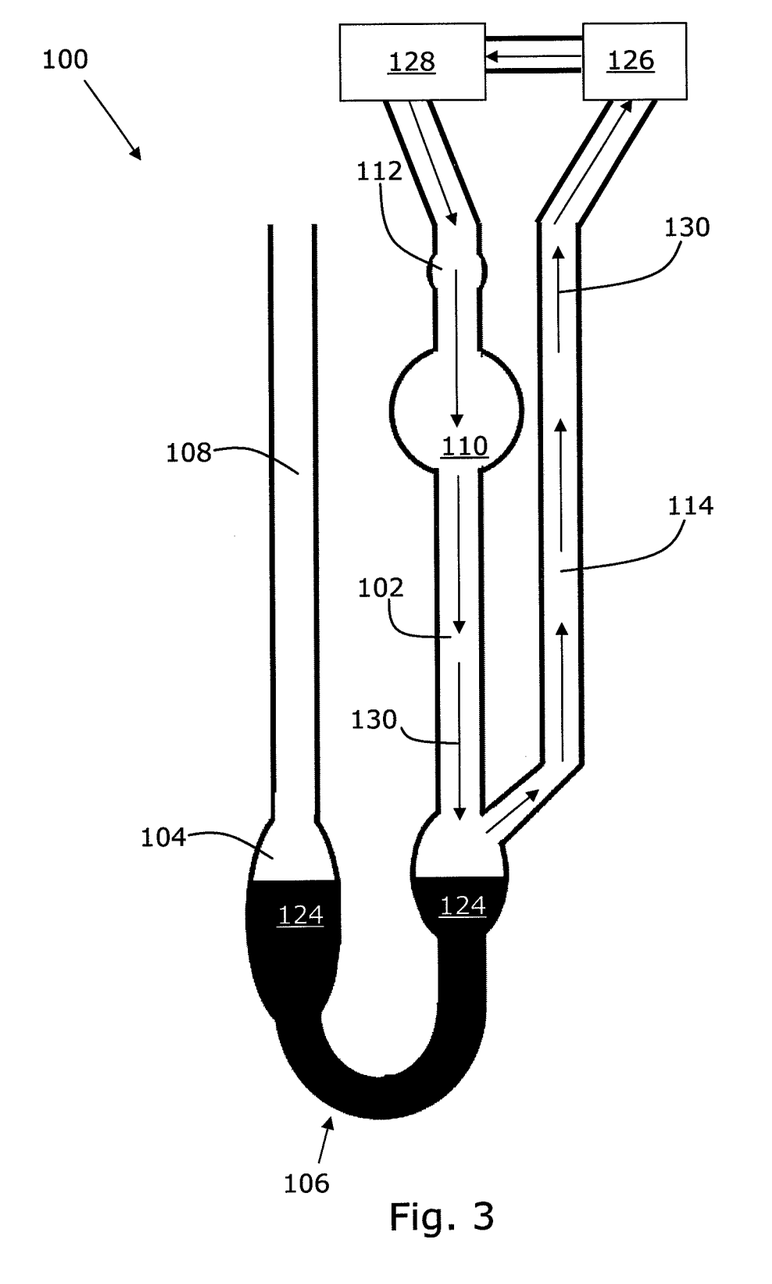

Once the liquid test sample 124 is provided in the viscometer 100, the air contained in the capillary tube 102 and the timing bulb 110 is dried by operating a pump 126. This is illustrated in FIG. 3. This causes the air contained in the capillary tube 102, the timing bulb 110 and the venting tube 114 to circulate as it is sucked into the pump 126 from which it is forced into the desiccant 128. The desiccant 128 removes vapour from the air which passes therethrough. Subsequently, the dried air is reintroduced into the timing bulb 110 and the capillary tube 102. The process is continued until enough vapour has been removed. The circulation of air is illustrated by arrows 130.

Figure 4:
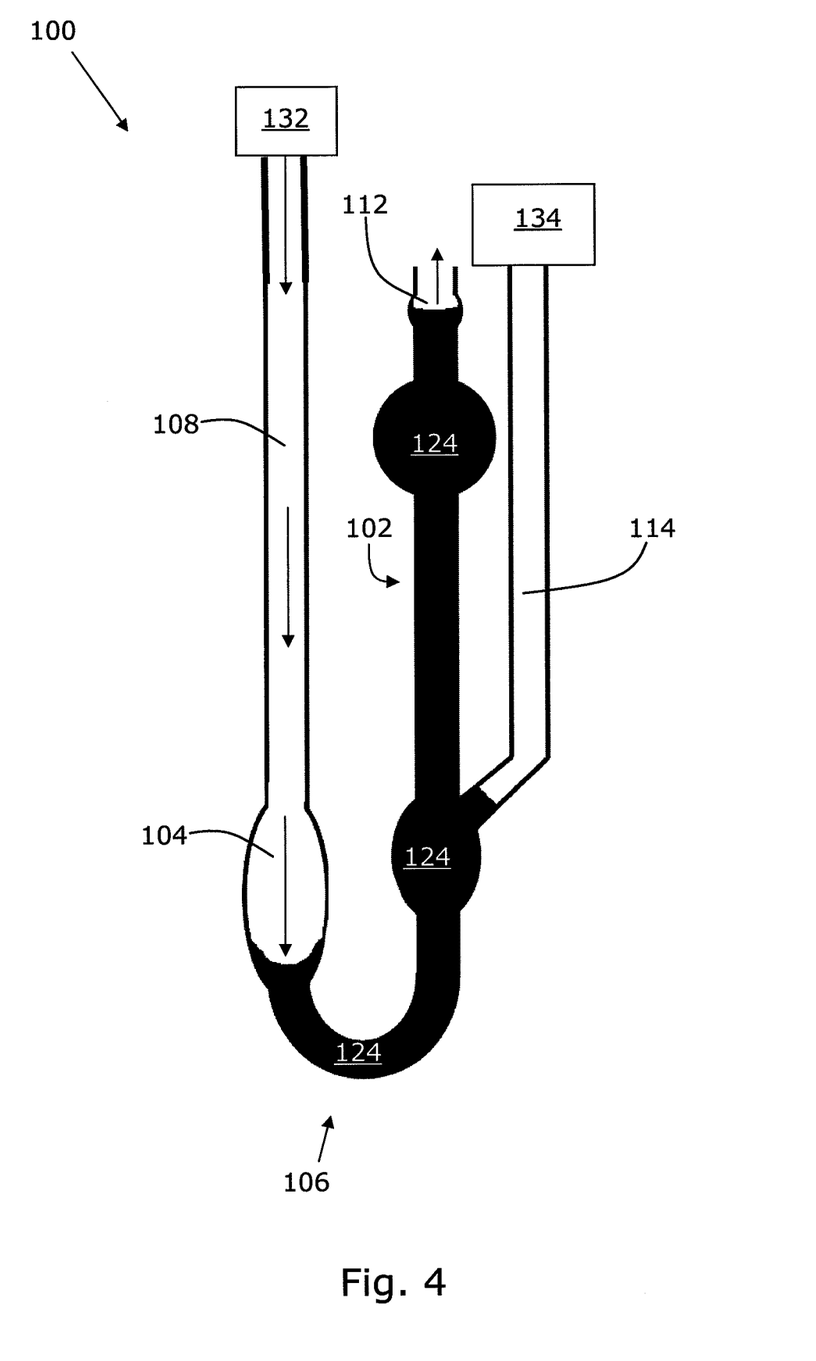

Once the air has reached the desired humidity, the liquid test sample 124 is moved into the capillary tube 102 and the timing bulb 110 as illustrated in FIG. 4. The liquid test sample 124 is forced into the capillary tube 102 and the timing bulb 110 by operation of a pump 132, which increases the pressure in the filling tube 108. Due to the increased pressure, the liquid test sample 124 is forced into the capillary assembly. In order to prevent the liquid test sample 124 from being forced into the venting tube 114, a valve 134 is provided. This valve is closed prior to and during operation of the pump 132. The pump 132 is operated at least until the meniscus passes the upper position 120 at which the upper sensor 116 is provided as is explained in relation to FIG. 1.

Subsequently, the temperature of the liquid test sample 124 is lowered to a sub-zero degrees Celsius temperature by means of the apparatus for controlling the temperature (not illustrated). As is described previously, this can be a container filled with a liquid for controlling the temperature.

Figure 5:
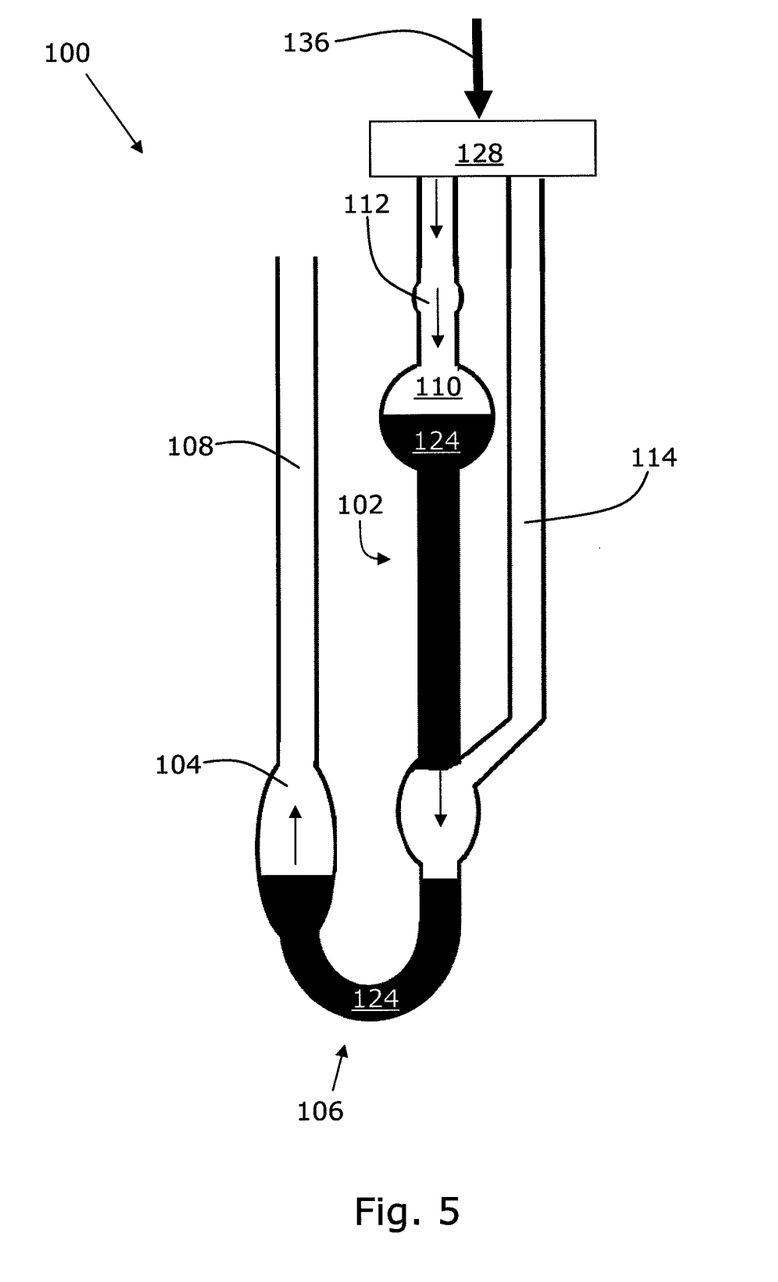

Once the temperature has reached the first sub-zero degrees Celsius temperature, the first viscosity is determined. This is illustrated in FIG. 5 in which the liquid test sample 124 is allowed to flow down through the capillary tube 102. During this process the first and second points in time are determined at which the meniscus passes the upper and the lower sensor 116,118 respectively. During this passage of the liquid test sample 124, air is allowed to flow into the capillary tube 102 and the timing bulb 110. In order to prevent air with a too high content of vapour from condensing on the inner surface of the capillary tube 102 and the timing bulb 110, the supplied air 136 may pass through a desiccant 128.

The steps are repeated until the temperature at which the predetermined viscosity has been determined.

The invention claimed is:

1. A viscometer adapted to determine a sub-zero degrees Celsius temperature at which a hydrocarbon, synthetic or semi-synthetic aviation fuel has a predetermined viscosity, the viscometer comprising:
    a capillary assembly comprising at least one of a capillary tube and a timing bulb;
    a sample reservoir fluidly connected to the capillary assembly;
    a built in apparatus to remove moisture in air in the viscometer;
    an air pump for advancing the liquid test sample from the sample reservoir to the capillary assembly; and
    an apparatus for controlling the temperature of the liquid test sample,
    wherein the temperature at which the viscosity is determined is a temperature below zero degrees Celsius, and
    wherein the built in apparatus removes the moisture before the air pump advances the liquid sample to the capillary assembly and prior to a measurement cycle.

2. The viscometer according to claim 1, further comprising a controller programmed to perform:
    a first step:
        in which the built in apparatus is operated so as to dry air contained in the viscometer, and
        in which the air pump is operated so as to advance the liquid test sample from the sample reservoir to the capillary assembly; and
    a second step:
        in which the apparatus for controlling the temperature of the liquid test sample is operated so as to change the temperature of the liquid test sample to a first temperature below zero degrees Celsius, and
        in which a first viscosity of the liquid test sample at the first temperature below zero degrees Celsius is determined.

3. The viscometer according to claim 2, wherein in the first step, the built in apparatus is drying operated while the temperature of the capillary assembly is above the dew point of the air contained in the viscometer.

4. The viscometer according to claim 2, wherein if the first viscosity is not the predetermined viscosity, the controller is adapted to perform
    a third step:
        in which the built in apparatus is operated so as to dry the air contained in the viscometer, and
        in which the pump is operated so as to advance the liquid test sample from the sample reservoir to the capillary assembly; and
    a fourth step:
        in which the apparatus for controlling the temperature of the liquid test sample is operated so as to change the temperature of the liquid test sample to a second temperature below zero degrees Celsius, and
        in which a second viscosity of the liquid test sample at the second temperature below zero degrees Celsius is determined.

5. The viscometer according to claim 4, wherein the controller is adapted to operate the air pump so as to advance the liquid test sample before operating the apparatus for controlling the temperature so as to change the temperature of the liquid test sample.

6. The viscometer according to claim 4, wherein the third and fourth steps are repeated at different temperatures below zero degrees Celsius until the predetermined viscosity is determined.

7. A method of operating a viscometer which comprises a capillary assembly, a sample reservoir fluidly connected to the capillary assembly, a built in apparatus to remove moisture in air in the viscometer, an air pump for advancing the liquid test sample from the sample reservoir to the capillary assembly, and an apparatus for controlling the temperature of the liquid test sample, the method comprising the steps of:

removing moisture in the air in the viscometer;

advancing the liquid test sample from the sample reservoir to the capillary assembly;

changing the temperature of the liquid test sample to a first temperature below zero degrees Celsius, and     determining a first viscosity of the liquid test sample at the first temperature below zero degrees Celsius,     wherein the built in apparatus removes the moisture before the air pump advances the liquid sample to the capillary assembly and prior to a measurement cycle.

8. The method according to claim 7, wherein the step of removing moisture is performed while the capillary assembly is above the dew point of air contained in the capillary assembly.

9. The method according to claim 7, further comprising the steps of drying the air contained in the capillary assembly;

advancing the liquid test sample from the sample reservoir to the capillary assembly; and     changing the temperature of the liquid test sample to a second temperature below zero degrees Celsius, and     determining a second viscosity of the liquid test sample at the second temperature below zero degrees Celsius.

10. The method according to claim 9, further comprising the steps of:

raising the temperature of the capillary assembly;

removing the liquid test sample from the capillary assembly; and     cleaning the capillary assembly.

11. The method according to claim 7, wherein the step of advancing the liquid test sample precedes the step of changing the temperature.

12. The method according to claim 7, wherein the steps are repeated at different temperatures below zero degrees Celsius until the predetermined viscosity is determined.

13. The method according to claim 7, further comprising the steps of:

raising the temperature of the capillary assembly;

removing the liquid test sample from the capillary assembly; and     cleaning the capillary assembly.

14. Use of a capillary assembly comprising at least one of a capillary tube and a timing bulb for determining a temperature at which a liquid test sample has a predetermined viscosity by means of the method according to claim 7.

15. The method according to claim 7, wherein the step of advancing the liquid test sample precedes the step of changing the temperature.

\* \* \* \* \*